US005376554A

United States Patent [19]

Vo-Dinh

[11] Patent Number: 5,376,554
[45] Date of Patent: Dec. 27, 1994

[54] APPARATUS AND METHODS FOR DETECTING CHEMICAL PERMEATION

[75] Inventor: Tuan Vo-Dinh, Knoxville, Tenn.

[73] Assignee: Martin Marietta Energy Systems, Inc., Oak Ridge, Tenn.

[21] Appl. No.: 938,119

[22] Filed: Aug. 28, 1992

[51] Int. Cl.$^5$ ............................................. G01N 33/00
[52] U.S. Cl. .................................................... 436/104
[58] Field of Search ............... 422/58, 82.05, 56, 57; 436/104, 102

[56] References Cited

U.S. PATENT DOCUMENTS 3,960,759  6/1976  Mallis .................................. 436/104
5,009,845  4/1991  Thoraval ........................... 422/57 X
5,192,693  3/1993  Yazawa et al. .................... 422/58 X

OTHER PUBLICATIONS

T. Vo-Dinh and D. A. White, "Development of Luminescence Procedures to Evaluate Permeation of Multi-Ring Polyaromatic Compounds Through Protective Materials," Am. Ind. Hyg. Asso. J. (48), Apr., 1987, pp. 400–405.
D. A. White and T. Vo-Dinh, "Room-Temperature Phosphorimetry to Study Petroleum Product Permeation Through Protective Clothing Materials," Applied Spectroscopy, V. 42, No. 2, 1988, pp. 285–288.
T. Vo-Dinh and T. Pal, "Development of a Fluorescence Quenching Technique to Detect Permeation of Chemical Agent Simulants through Protective Clothing Materials," Applied Spectroscopy, V. 46, No. 4, 1992, pp. 677–681.

Primary Examiner—Peter Nerbun
Attorney, Agent, or Firm—Shelley L. Stafford; Joseph A. Marasco; Harold W. Adams

[57] ABSTRACT

Apparatus and methods for detecting the permeation of hazardous or toxic chemic AppaRU,VPE protective clothing are disclosed. The hazardous or toxic chemicals of interest do not possess the spectral characteristic of luminescence. The apparatus and methods utilize a spectrochemical modification technique to detect the luminescence quenching of an indicator compound which upon permeation of the chemical through the protective clothing, the indicator is exposed to the chemical, thus indicating chemical permeation.

20 Claims, 11 Drawing Sheets

APPARATUS AND METHODS FOR DETECTING CHEMICAL PERMEATION

This invention was made with Government support under contract DE-AC0584OR21400 awarded by the U.S. Department of Energy (DOE) to Martin Marietta Energy Systems, Inc., and the Government has certain rights in this invention.

This work was also sponsored by the Office of Assistant Secretary for Installations, Logistics and Environment, U.S. Department of the Army (IAG #DOE 1769-1354-A1), by the Office of Natural and Technological Hazards Federal Emergency Management Agency (IAG #1457-B106-A1), and the DOE Office of Health and Environmental Research.

FIELD OF THE INVENTION

The present invention relates to apparatus and methods for detecting the permeation of a chemical through a material acting as a barrier, and in particular, the permeation of a hazardous or toxic chemical through a protective material. The present invention also relates to the fabrication of protective clothing materials.

BACKGROUND OF THE INVENTION

The Chemical Stockpile Emergency Preparedness Program (CSEPP) has been established by the Department of the Army's Office of Program Manager for Chemical Demilitarization to carry out Congressional mandates of 1986 and 1988. The first mandate, the Department of Defense Authorization Act of 1986 (PL 99-145), directed and authorized the Secretary of Defense to destroy the United States stockpile of lethal unitary chemical munitions and agents by Sep. 30, 1994; the Act was amended in 1988 (PL 100-456) to permit operations testing of a commercial scale incinerator design and to allow for unitary munitions disposal completion by April 1997. The inventory of material to be destroyed includes the organophosphate nerve agents GA, GB, and VX, as well as the vesicant (blister) agents H, HD, HT (various formulations of sulfur mustard), and Lewisite (an organic arsenical).

There is great concern regarding skin exposure to these chemical warfare agents for personnel involved in handling and disposing of these species, as well as those civilian emergency personnel who may need to respond to an unplanned agent release. The degree of protection provided civilian emergency workers in a chemical agent environment is a current unknown due to the untested status of readily available protective clothing. Methods are needed to determine which materials can be used as protective barriers against hazardous or toxic chemical warfare agents.

Furthermore, many hazardous and toxic chemicals are not easily detected by conventional techniques such as luminescence, normal Raman or infrared spectroscopics. There is a strong need to develop practical methods for monitoring these chemicals for environmental and human exposure protection.

The experimental sampling protocol of the subject invention is based on two previous works characterizing the permeation of petroleum products through protective clothing materials using luminescence techniques for detecting polycyclic aromatic compounds (PAC) contained in the petroleum products. A method which uses room temperature phosphorescence (RTP) was reported by T. Vo-Dinh and D. A. White, "Room Temperature Phosphorimetry to Study Petroleum Product Permeation Through Protective Clothing Materials," *Applied Spectroscopy* 42(1988), 285–288. A method using fluorescence techniques was also reported by T. Vo-Dinh and D. A. White, "Development of Luminescence Procedures to Evaluate Permeation of Multi-Ring Polyaromatic Compounds Through Protective Materials," *J. Amer. Industrial Hygiene Assoc.* 48(1987), 400–405. However, since the chemicals of interest in the subject invention do not contain PAC and are not strongly fluorescing and/or phosphorescing, a novel and sensitive spectroscopic method for the detection of permeation and breakthrough time using spectroscopic modification of an indicator compound is presented.

SUMMARY OF THE INVENTION

Accordingly, it is an object of the present invention to provide new and improved methods for protecting the environment and humans.

It is another object of the invention to provide new and improved methods and apparatus for detecting the permeation of a chemical through a material acting as a protective barrier.

It is a further object of the invention to provide new and improved methods and apparatus for detecting the permeation of a hazardous or toxic chemical through a protective material.

It is another object of the invention to provide new and improved methods and apparatus for detecting the failure of protective clothing.

It is a further object of the invention to provide new and improved methods for fabrication and design of protective clothing materials.

Further and other objects of the present invention will become apparent from the description contained herein.

In accordance with one aspect of the present invention, the foregoing and other objects are achieved by a general apparatus for detecting the permeation of a chemical through a material which comprises a material, a contacting means, and an analyzing means. The material has first and second surfaces wherein the first surface is treated with an indicator. The indicator possesses spectral characteristics which are modified upon contact with the chemical. The second surface of the material is in contact with the chemical. The analyzing means determines the modification of spectral characteristics of the indicator in order to detect permeation of the chemical through the material.

In accordance with another aspect of the invention, a new and improved apparatus for detecting the permeation of a chemical through a material comprises a material, a substrate, a contacting means, and an analyzing means. The material has a first surface and a second surface, the first surface being adjacent to the substrate and the second surface contacting the chemical by use of the contacting means. The substrate is treated with an indicator having spectral characteristics which are modified upon contact with the chemical. The analyzing means determines the modification of spectral characteristics of the indicator in order to detect permeation of the chemical through the material.

In accordance with a further aspect of the present invention, an article of protective clothing adapted for detecting the permeation of a chemical through the article comprises an article of protective clothing material and an indicator having spectral characteristics which are modified upon contact with the chemical. The article of protective clothing material has an inner surface and an outer surface. The indicator is supported on the inner surface of the article of protective clothing material.

In accordance with a still further aspect of the present invention, an article of protective clothing adapted for detecting the permeation of a chemical through the article comprises an article of protective clothing, a substrate, and an indicator having spectral characteristics which are modified upon contact with the chemical. The article of protective clothing has an inner surface and an outer surface. The substrate, which supports the indicator, is secured to the inner surface of the article of protective clothing material so that upon permeation of the chemical through the article, the chemical will contact the substrate, modifying the spectral characteristics of the indicator, indicating permeation of the chemical through the article of protective clothing.

In accordance with yet another aspect of the present invention, a new and improved method for detecting the permeation of a chemical through a material comprises the steps of:

Step 1. Providing a material with a first surface and a second surface.

Step 2. Treating the first surface with an indicator having spectral characteristics which are modified upon contact with the chemical.

Step 3. Contacting the second surface of the material with the chemical.

Step 4. Determining the modification of spectral characteristics of the indicator in order to detect permeation of the chemical through the material.

In accordance with yet another aspect of the present invention, a method for detecting the permeation of a chemical through a material comprises the steps of:

Step 1. Providing a material with a first surface and a second surface. The first surface is adjacent to a substrate.

Step 2. Treating the substrate with an indicator having spectral characteristics which are modified upon contact with the chemical.

Step 3. Contacting the second surface of the material with the chemical.

Step 4. Determining the modification of spectral characteristics of the indicator in order to detect permeation of the chemical through the material.

In accordance with another aspect of the present invention, a method for adapting an article of protective clothing for detecting the permeation of a chemical through the article comprises the steps of:

Step 1. Providing an article of protective clothing material having an inner surface and an outer surface.

Step 2. Providing an indicator supported on the inner surface of the material and having spectral characteristics which are modified upon contact with the chemical so that upon permeation of the chemical through the article, the chemical will contact the indicator, indicating permeation of the chemical through the article of protective clothing.

In accordance with yet another aspect of the present invention, a method for adapting an article of protective clothing for detecting the permeation of a chemical through the article comprises the steps of:

Step 1. Providing an article of protective clothing having an inner surface and an outer surface.

Step 2. Providing a substrate secured to the inner surface, the substrate supporting an indicator having spectral characteristics which are modified upon contact with the chemical, so that upon permeation of the chemical through the article, the chemical will contact the substrate, indicating permeation of the chemical through the article of protective clothing.

BRIEF DESCRIPTION OF THE DRAWINGS

For a better understanding of the present invention, together with other and further objects, advantages and capabilities thereof, reference is made to the following disclosure and appended claims when read in connection with the appended drawings, wherein:

DETAILED DESCRIPTION OF THE INVENTION

Figure 1:
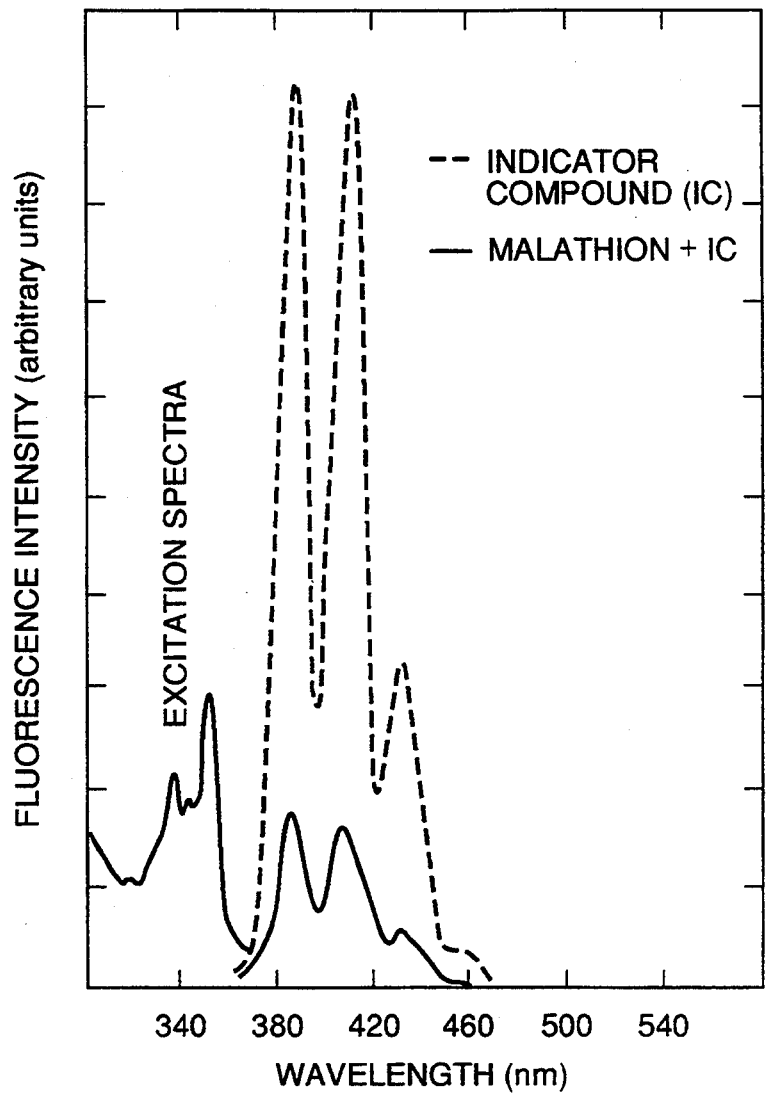
FIG. 1 shows Fluorescence Quenching of Phenanthrene by Malathion, excited at 352 nm.

The subject invention is a novel yet practical approach for detecting the permeation of hazardous and toxic chemicals through protective clothing material, to indicate failure thereof. The invention is based on a spectrochemical modification (SM) technique in which an indicator compound when contacted by a nonluminescent chemical compound of interest has its spectral characteristic of luminescence changed. The SM technique is applied to detect the permeation of a variety of hazardous and toxic chemicals through protective clothing materials. The SM technique as applied to the subject invention involves the detection of spectrochemical modification, such as luminescence quenching, of an indicator compound in the presence of chemical compounds of interest.

The chemical compounds of interest as related to the present invention include hazardous or toxic chemicals that are toxic upon contact with the skin, that do not possess the indicated spectral characteristic of luminescence. These chemical compounds comprise chemical warfare agents, chemical warfare agent simulants, agricultural chemicals, biopharmaceutical chemicals as well as hazardous waste chemicals. Chemical warfare agents are of two types, the organophosphate nerve agents and the vesicant (blister) mustard agents. The organophosphate nerve agents comprise Agent GA, also called Tabun (Ethyl-N,N-dimethylphosphoramidocyanidate) Agent GB, also known as Sarin (O-isopropylmethylphosphonofluoridate); Agent GD or Soman (O-pinacotylmethylphosphonofluoridate); and Agent VX (O-ethyl-S-(2-diisopropylaminoethyl)methylphosphonothiolate). The vesicant (blister mustard) agents comprise Agents H, HD, and HT (various formulations of sulfur mustard), as well as Lewisite (dichloro[2-chlorovinyl]arsine). Sulfur mustard (bis[2-chloroethyl]-sulfide) is the principal vesicant component of agents H (Levinstein mustard); HD (distilled mustard), and HT (a plant-run mixture of about 60% HD, <40% stabilizer "T" [bis(2-chloroethylthioethyl)ether], and a variety of sulfur impurities). The chemical warfare agent simulants comprise DMMP, a VX agent simulant; DBS, a sulfur mustard simulant; DIMP, GB agent simulant; and MAL, a nerve agent simulant. Agricultural chemicals of interest as related to the subject invention also comprise organophosphates used as pesticides, such as malathion. Biopharmaceutical chemicals of interest also overlap, comprising organophosphates used in the synthesis of pharmaceutical products. Hazardous waste chemicals of interest as related to the subject invention comprise the stockpile of chemical warfare agents as well as the wastes generated from the agricultural chemical industry and the biopharmaceutical industry.

The detection of the quenching effect on the luminescence of the indicator compound is an important aspect of the invention. Through extensive measurements using a wide variety of compounds, such as pyrene, naphthalene, anthracene, emodin, indole, fluorescein and diphenylamine, it was found that phenanthrene and its alkylated derivatives, such as 4-methylphenanthrene or 1-butylphenanthrene, were unique compounds that could be used for detecting the presence of chemical warfare agent simulants. Since they were the best indicators for detecting the presence of chemical warfare agent simulants, they would be the best indicators for detecting other similar chemicals that lacked the spectral characteristic of luminescing. Measurements of luminescence quenching of phenanthrene used as the indicator compound yielded excellent results for detecting chemical agents adsorbed on exposed filter paper substrates, see FIG. 1.

FIG. 1 shows the fluorescence signal of phenanthrene on filter paper with and without malathion. Phenanthrene is a three-benzene ring polyaromatic hydrocarbon that has the longest absorption at approximately 345–355 nm. The excitation at 352 nm used in this investigation was therefore absorbed directly by phenanthrene, which exhibits fluorescence emission in the 380–470 nm range. Excitation at higher energies can be selected to coincide with strong absorption bands of phenanthrene: $S_2$ singlet state at 34,200 cm$^{-1}$ (292 nm) with $\epsilon=14800$, $S_3$ state at 39,900 cm$^{-1}$ (250 nm) with $\epsilon=67,000$, and $S_4$ state at 47,300 cm$^{-1}$ (211 nm) with $\epsilon=35,500$. The decrease of the intensity of phenanthrene caused by the quenching process is clearly observed in FIG. 1. The spectral profile of phenanthrene fluorescence following quenching by malathion (FIG. 1, solid curve) remained similar to that of unquenched phenanthrene (FIG. 1, dashed curve).

Both spectra consist of a principal series of four vibronic bands of diminishing intensities, equally spaced at energy intervals of approximately 1400 cm$^{-1}$, which correspond to the frequency of the dominant C—C vibrational modes. The similarity of the fluorescence spectra in FIG. 1 indicates that malathion induced quenching but did not alter the chemical structure of phenanthrene, which would have made visible energy changes in the excited singlet state (e.g., spectral shift of the O—O band or change of vibronic bands). Furthermore, intensity distribution of the two spectra in FIG. 1 also indicated that interaction with malathion did not induce significant changes in the relative positions (i.e., Stokes shift) of the energy potentials of the ground and excited state.

Figure 2:
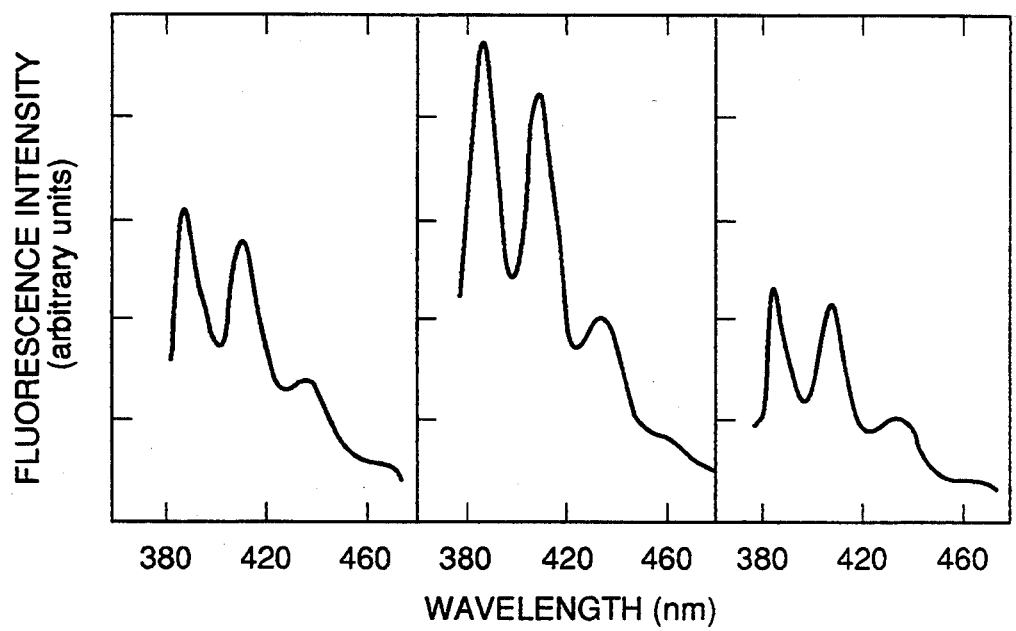
FIG. 2 illustrates the Spectrochemical Modification Technique applied to diisopropylmethylphosphonate (DIMP), dimethylmethylphosphonate (DMMP), and dibutylsulfide (DBS), chemical agent simulants.

FIG. 2 illustrates the fluorescence spectra of phenanthrene ($10^{-2}$ M) following interaction with DBS, DIMP and DMMP at an excitation of 352 nm. The fluorescence spectrum of phenanthrene ($10^{-2}$ M) alone under similar conditions is shown previously in FIG. 1. The results indicate that the SM technique can be used to indicate the interaction of DBS, DIMP and DMMP with phenanthrene by detecting the fluorescence quenching effect.

Figure 3:
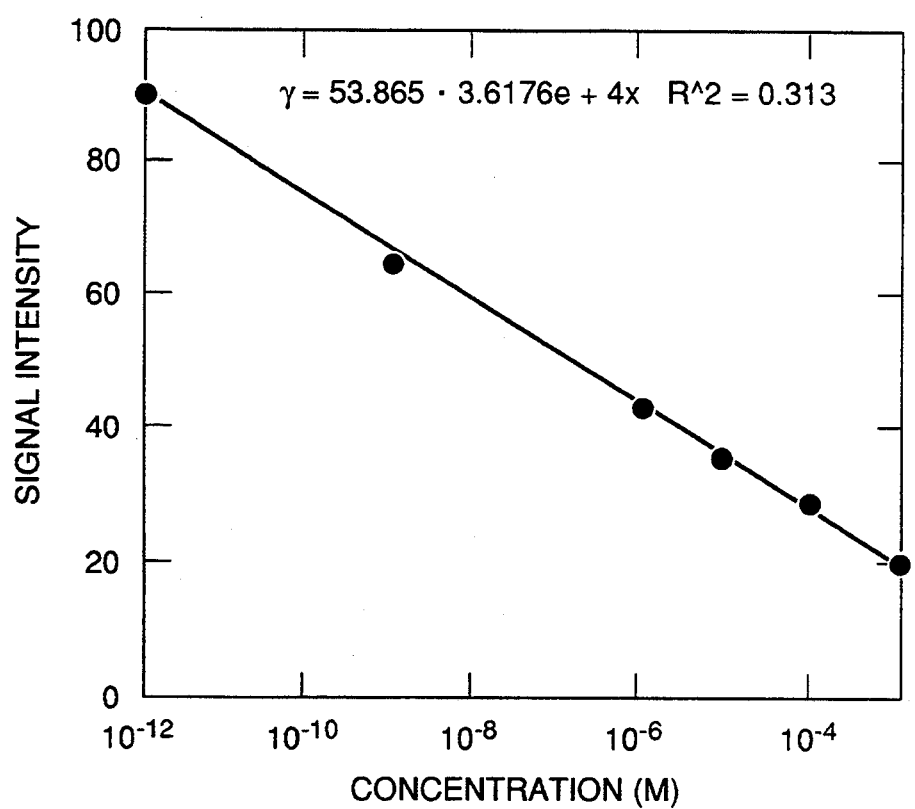
FIG. 3 is a calibration curve for quantitative detection of DMMP.
Figure 4:
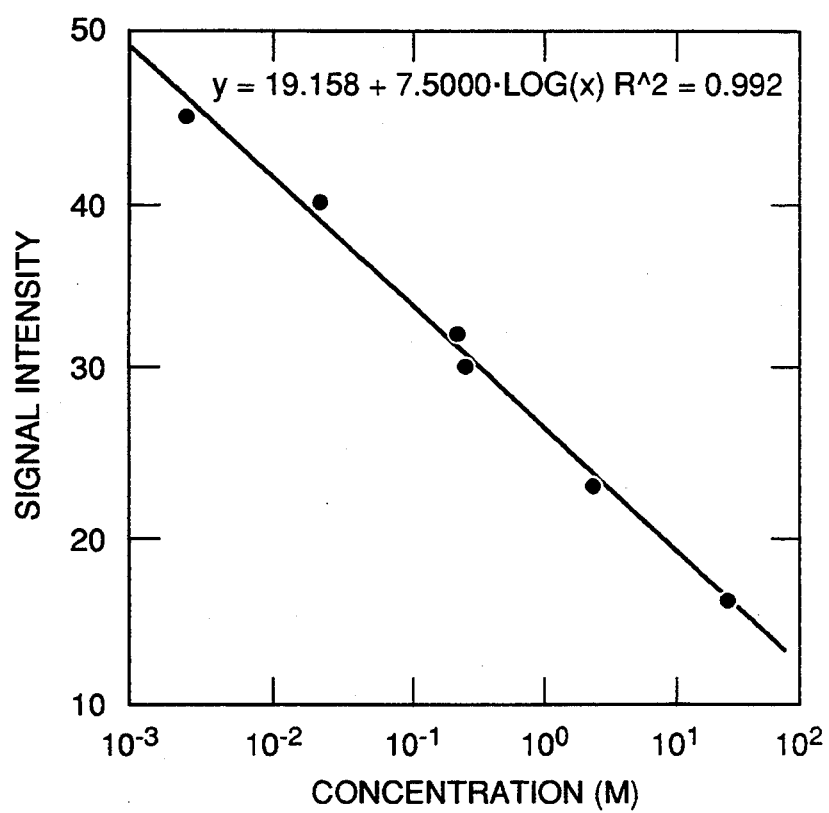
FIG. 4 is a calibration curve for quantitative detection of malathion (MAL).

FIG. 3 shows the quantitative calibration curve relating the quenching effect of phenanthrene fluorescence to the concentration of chemical agent simulants. In this series of experiments, the concentration of the indicator compound (phenanthrene) was kept constant ($2.3\times10^{-2}$ M), and the amount of the analyte (DMMP) was varied over 5 orders of magnitude (spot sample from 0.1 ng to 10 $\mu$g). The results shown in FIG. 3 indicate that there is a direct relationship between the extent of fluorescence quenching and the amount of DMMP added to the sample spot of phenanthrene. The results show an inverse relationship between the fluorescence intensity of the indicator compound and the logarithm of the concentration of the analyte compound (i.e., DMMP). The results displayed in FIG. 3 demonstrate that the SM technique developed for use with this invention can provide a practical and efficient tool to quantitatively detect the amount of analyte. FIG. 4 shows another example of quantitative analysis employing the quenching effect of the indicator compound (phenanthrene) by another analyte, malathion.

Figure 5:
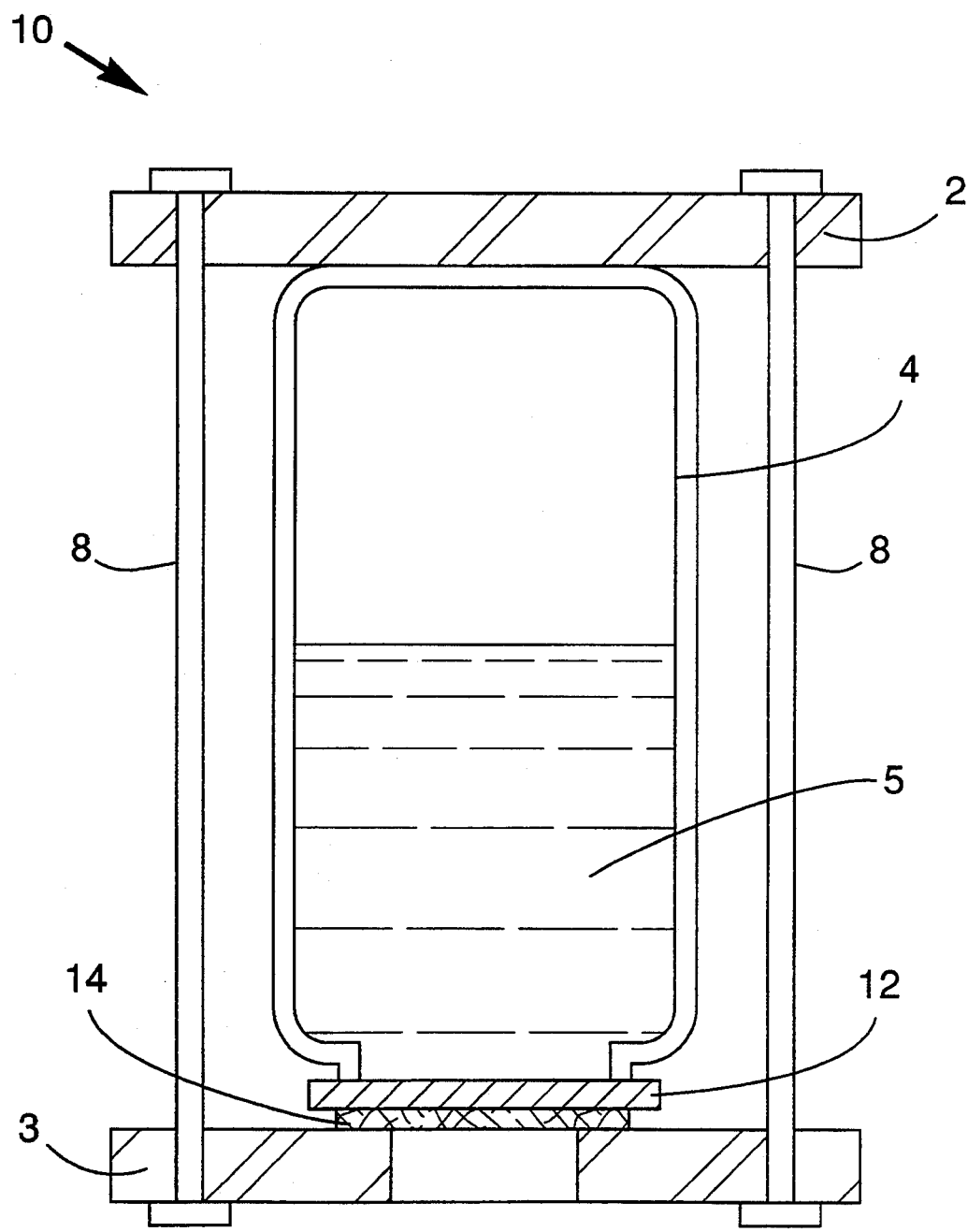
FIG. 5 is a sectional view of a laboratory apparatus used to measure the permeation of hazardous and toxic chemicals through protective clothing materials.

One embodiment of the invention is illustrated in FIG. 5. FIG. 5 shows a laboratory apparatus 10 comprising an open-ended cell 4, containing a liquid 5, a disc of protective clothing material 12, a cellulose substrate (e.g., filter paper patch) 14 treated with a solution of indicator, a solid support plate 2 and a support plate 3 having an opening in the center. The opening prevents any interference that may occur between the support plate 3 and the indicator compound on the substrate. The assembly is held together by screw clamps 8. Contact between the chemical and the protective clothing material is achieved by inverting the assembly to the position shown in FIG. 5. Another embodiment of the invention contacts the protective clothing material with an atmosphere containing the hazardous or toxic chemical in the gas phase. Example 1 describes the use of the apparatus while used to monitor permeation of several chemical agent simulants through a variety of protective clothing materials by analyzing the surface of a cellulose substrate (e.g., a filter paper patch) treated with a solution of phenanthrene indicator ($10^{-2}$ M), to determine the rate at which chemicals permeated through the protective clothing materials.

EXAMPLE 1

A disc of the protective clothing material 12 was positioned over the open end of a cell (e.g., glass) 4 containing approximately 1 mL of the chemical agent simulant 5, as shown in FIG. 5. A 2.0 cm diameter disc of filter paper 14 treated with the indicator compound was centered over the area of permeation, in contact with the protective clothing material 12. To prepare the filter paper for exposure, the disc was mounted on the sample holder as in FIG. 5, positioned over the center opening of the support plate 3. Once the paper was positioned, it was then spotted with 2.5 $\mu$L of the indicator compound (phenanthrene) in a solution of ethanol, followed by a drying period of 3 minutes under an infrared heating lamp. The exposure setup, consisting of the open-ended cell, the disc of protective clothing material, and the filter paper patch treated with the indicator compound, was mounted between the two support plates, 2 and 3, and clamped down by screws 8, to ensure a seal between the protective clothing material and the cell. To initiate a permeation measurement, the cell was inverted to the position shown in FIG. 5, so that the chemical agent challenged the surface of the protective clothing sample. After the desired exposure time, the filter paper disc was removed and analyzed directly by measuring the extent of luminescence quenching of the indicator compound in order to determine the presence and quantify the amount of chemical. No chemical extraction was necessary for the analysis.

Figure 13:
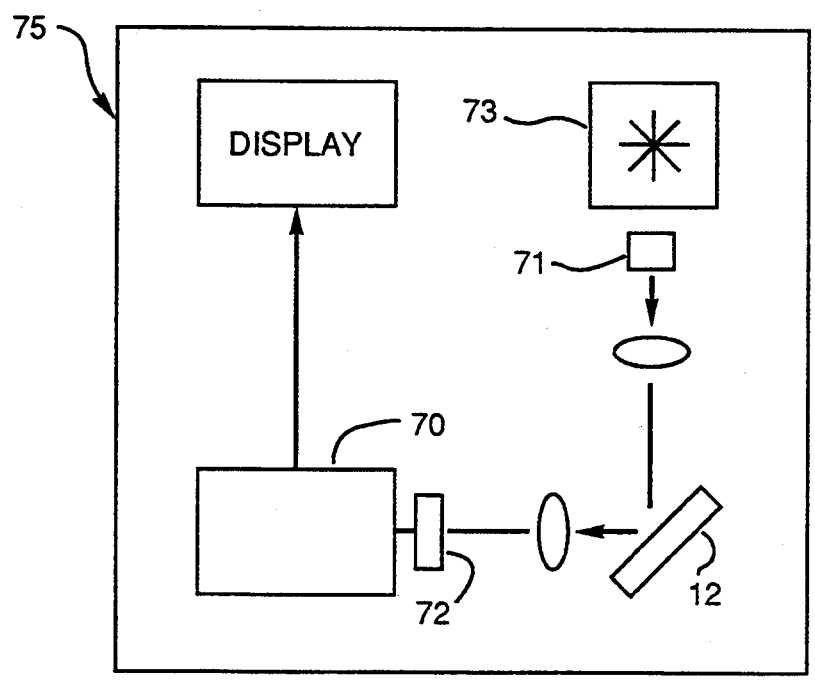
FIG. 13 shows a spectrofluorometer analyzing means.

Referring to FIG. 13, the luminscence measurements were made with two Perkin-Elmer spectrofluorometers 75. Model 43A and Model 650 (Perkin-Elmer, Norwalk, Conn.). The excitation light sources 73 were a continuous-wave (CW) 150-W xenon arc lamp and a pulsed 6-W xenon lamp for the Model 43-A and Model 650, respectively. The detector 70 was an R777 photomultiplier (Hamamatsu Company, Middlesex, N.J.) that has a spectral response from 185 to 850 nm. A spectral bandwidth of 10 nm was used for the excitation and emission monochromators 71, 72.

The protective clothing materials were obtained from commercially available sources. Whatman ® (Whatman International Ltd., Maidstone, England) No. 42 filter paper was used as the sorbent medium substrate for the chemical warfare agent simulants permeating through the protective clothing material. The chemical warfare agent simulants were purchased at their highest purity available and used without further purification. There were four chemical warfare agent simulants used: DBS (Aldrich), DIMP (Alpha Products), DMMP (Johnson Matthey Electronics), and malathion (MAL, Inc.).

Figure 6:
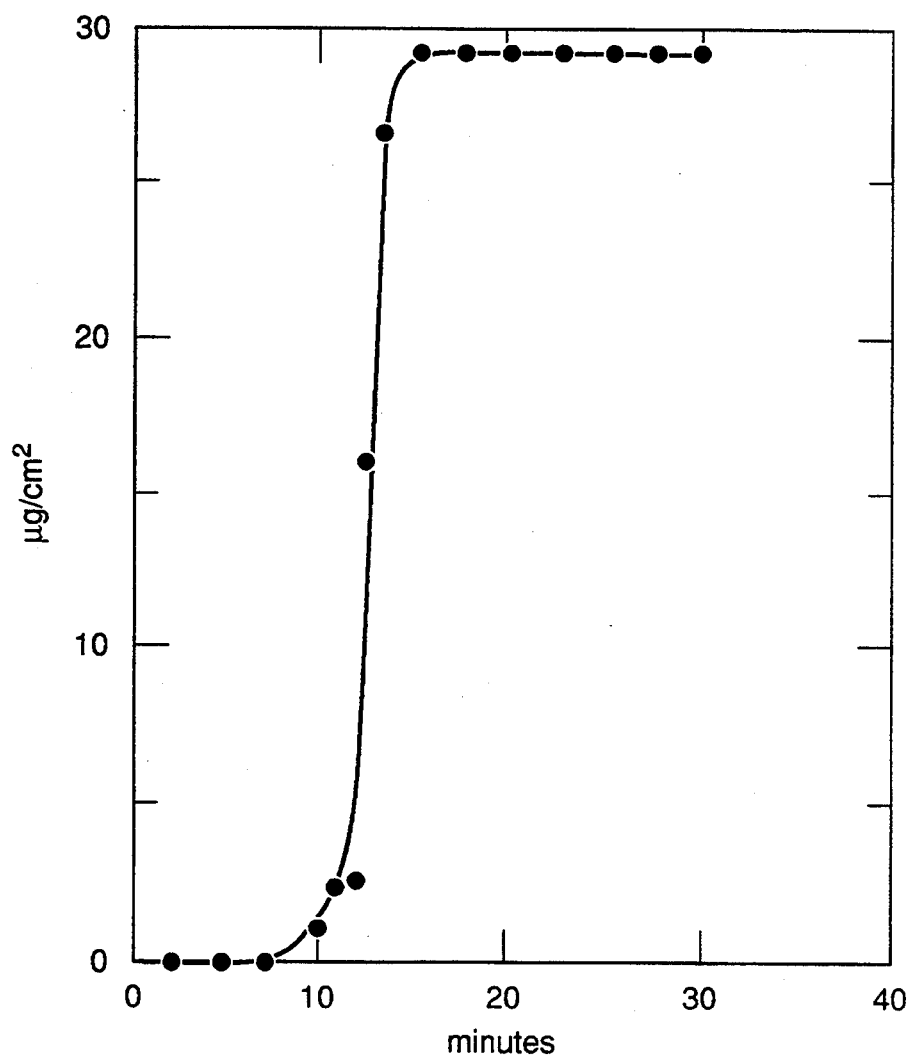
FIG. 6 shows results of permeation study of DBS through neoprene plastic glove material.
Figure 7:
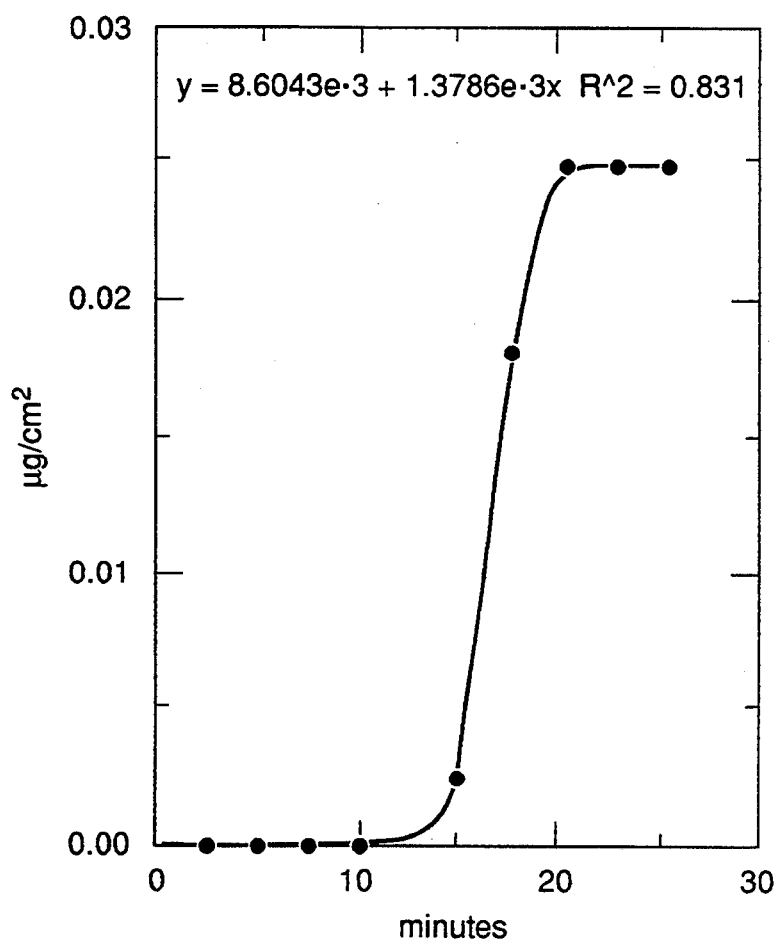
FIG. 7 shows results of permeation study of DMMP through neoprene plastic glove material.

Extensive luminescence quenching measurements were performed to determine the rate at which chemicals permeated through a variety of protective materials. The experiments also provided the individual breakthrough times for each chemical. FIGS. 6 and 7 illustrate the results of experiments in which luminescence quenching measurements were performed on phenanthrene exposed to permeation of DBS and DMMP through neoprene plastic for progressive 15-minute intervals over an 8-hr challenge period. These calibration plots illustrate the fluorescence intensities as a function of permeation, using the emission and excitation wavelengths at 390 and 325 nm, respectively. The emission signals were recorded at 410 nm using a 10 nm spectral bandwidth. In these experiments, the breakthrough time was defined as the time required for the first detectable (by fluorescence quenching) quantity of challenge compound to permeate through the protective clothing materials onto the filter paper treated with phenanthrene. An example of breakthrough time studies for DIMP through several protective materials is summarized in Table 1.

TABLE 1

PERMEATION OF DIMP THROUGH SEVERAL PROTECTIVE MATERIALS

| Type of Protective Materials | Breakthrough Time |
| --- | --- |
| Polyvinyl Chloride (PVC)/Nylon/PVC ("305 PCV/BA," Fyrepel Products) (Newark, OH) | 10 min |
| Butyl/Nitrile glove material ("Pioneer Gatorhide," Pioneer Industrial Products) (Willard, OH) | 1 h |
| Teflon/Kevlar/Teflon "Force Field TM," Fryepel Products (Newark, OH) | >24 h |
| Tyvek (a spunbonded olefin material) Kappaler Safety Group (Guntersville, AL) | 30 min |
| Neoprene plastic glove material (Playtex, ®) (International Playtex, Inc., Stamford, CT) | 45 min |

A comparison of the two different emission spectral curves illustrated in FIG. 6 (DBS through neoprene plastic) and FIG. 7 (DMMP through neoprene) reveals noticeable differences in breakthrough times. In particular, breakthrough in FIG. 7 occurs later (15 min after the beginning of exposure) and at a significantly slower rate than that shown in FIG. 6 (10 min). The curves in FIGS. 6 and 7 illustrate the utility of the luminescence quenching measurements to determine permeation rates for various compounds. Quantitative calibration involving normalization against the quenching of the indicator compound luminescence by known amounts of specific chemicals can provide quantitative information about the breakthrough curves and rates of permeation of specific compounds of interest. With a standard challenge time, the luminescence quenching technique may be used as a practical and cost-effective testing protocol to provide a preliminary ranking which can serve as a guide for more detailed studies of breakthrough times and rates of penetration of chemical agents through protective materials.

Figure 8:
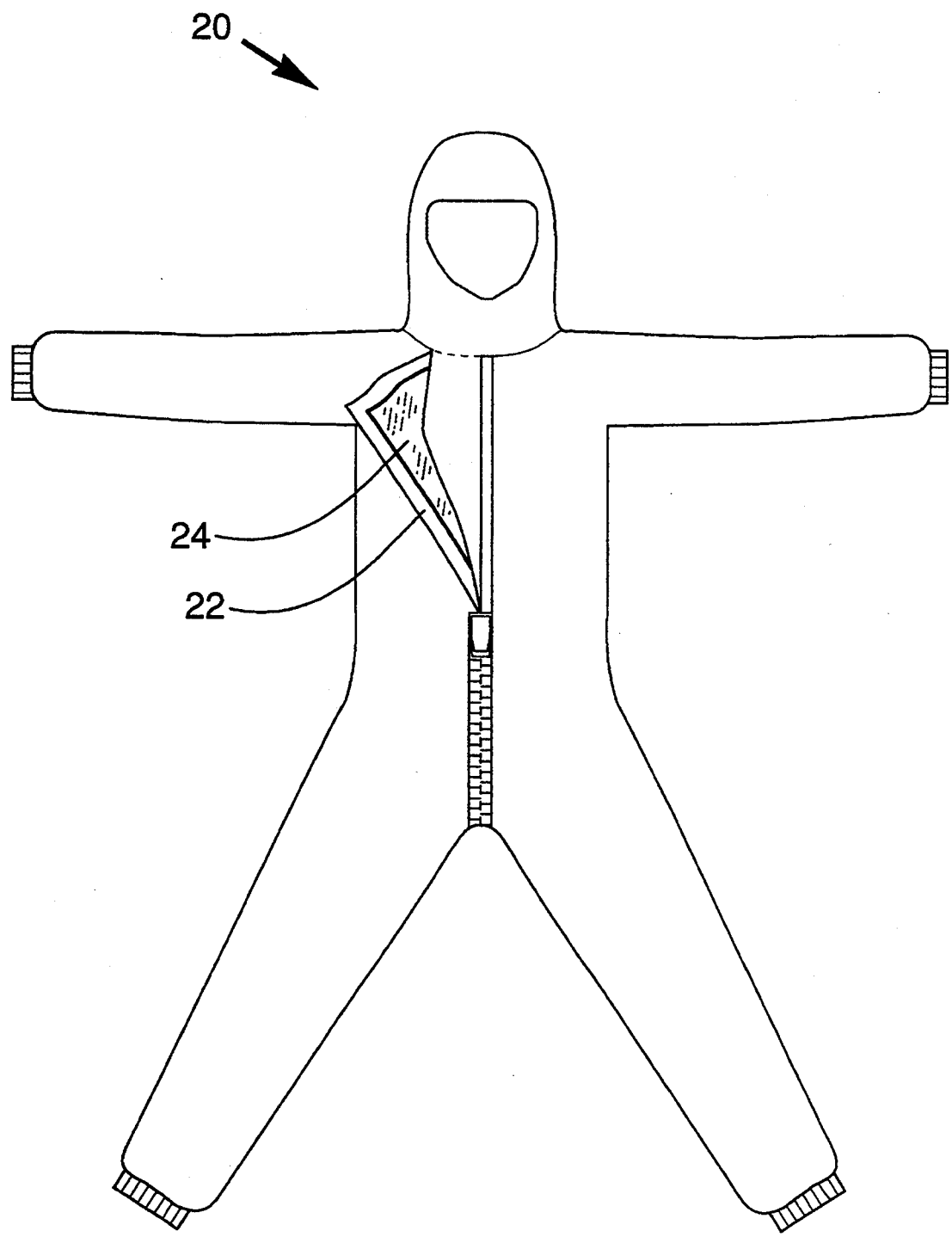
FIG. 8 is a schematic diagram of a multi-layer article of protective clothing with a corner of the clothing turned back to show the multiple layers of the fabric.

Another aspect of the invention is shown in FIG. 8, a schematic diagram of a multilayer article of protective clothing 20 with a corner of the clothing turned back from the inside out to demonstrate the multiple layers of the fabric. The protective material layer 22 throughout the entire article of protective clothing has previously been treated with an indicator compound (e.g., phenanthrene) before the transparent layer (e.g., transparent polymer, such as plastic) 24 is applied as a protective covering for the indicator compound. The transparent layer while acting as a protective covering also acts as an optically transparent window to allow for direct spectral analysis of the indicator compound. The transparent layer is applied permanently to the inner surface of the indicator-treated fabric using a binding agent, such as an adhesive, along the borders. The inner surface of the fabric is treated with the indicator by spotting, spraying or impregnating the fabric with the indicator compound solution. After a drying period under an infrared heating lamp, the fabric is ready for the application of the transparent layer. The article of protective clothing is worn with the transparent cover on the inside, adjacent the person's body, with the outer surface of the fabric exposed to the environment. The indicator compound is protected by the transparent layer.

Another method for adapting the multi-layer article of protective clothing for permeation detection is to spray on a coating of a transparent polymer directly onto the inner surface of the protective material supporting the indicator compound. The coating acts as a protective cover for the indicator compound as well as an optically transparent window for direct spectral analysis of the indicator.

Figure 9:
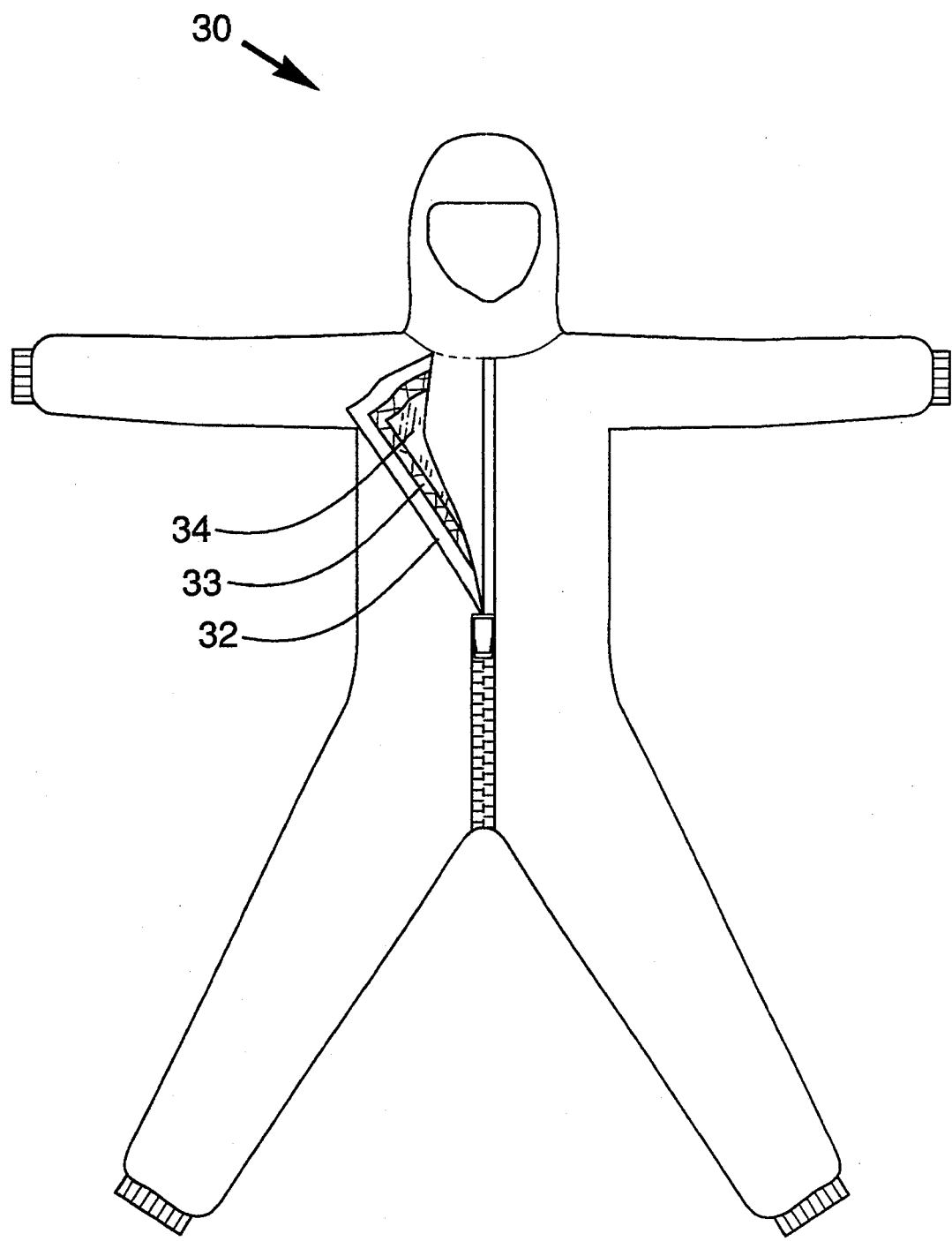
FIG. 9 is another embodiment of a multi-layer article of protective clothing in which a separate and additional substrate layer supporting the indicator compound is added.

FIG. 9 illustrates another embodiment of the multi-layer article of protective clothing. The multi-layer article 30 comprises a protective clothing material layer 32, a substrate 33, which supports the indicator compound (e.g., phenanthrene), and a transparent layer 34 which acts as a protective cover for the indicator-treated substrate while acting as an optically transparent window to allow direct spectral analysis of the indicator. The substrate is generally a cellulosic material such as paper or a sorbent material, such as alumina, metal oxide, activated carbon or other carbon material. The substrate is dipped into or is impregnated with the indicator compound solution for quick and easy mass production. The substrate is secured permanently to the inner surface of the protective material, using a binding agent, such as an adhesive, along the borders. The transparent layer is a transparent polymer, such as plastic, that is secured permanently to the substrate along the borders using a binding agent (e.g., an adhesive).

Another method for adapting the multi-layer article of protective clothing for permeation detection is to spray on a coating of a transparent polymer directly onto the indicator-treated substrate until it coats the entire surface, to protect the indicator compound and to act as an optically transparent window for direct spectral analysis of the indicator compound. The multi-layer embodiment of FIG. 9 is also worn with the outer surface of the protective material exposed to the environment and the transparent cover worn on the inside, adjacent the person's body.

The articles of protective clothing of FIGS. 8 and 9 provide full body protection with the use of gloves, boots, a face mask and breathing apparatus. Both embodiments of multilayer protective clothing are effective for quick detection of the permeation of any hazardous or toxic vapors or liquid. The two embodiments of the multi-layer protective clothing act as real-time monitors of the permeation of hazardous or toxic vapors or liquids. At the end of the exposure period, when the multi-layer article of protective clothing is shed from the wearer's body, the indicator compound is then analyzed for luminescence quenching. Using the optically transparent window, the luminescence measurements are made with a portable luminescence monitor such as the fiber-optics luminoscope available from Environmental Systems Corp., Knoxville, Tenn.

Figure 10:
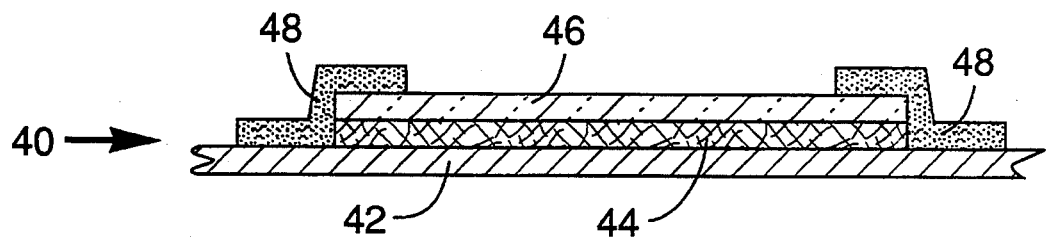
FIG. 10 is a cross-sectional view of a patch illustrating yet another embodiment of the invention.

FIG. 10 is a cross-sectional view of yet another aspect of the invention. A patch is shown comprising a protective clothing material 42, substrate 44 treated with an indicator compound (e.g., phenanthrene), a transparent layer 46 covering and protecting the indicator compound and a securing means 48, such as an adhesive or other binding agent, to secure the transparent layer and the substrate to the protective material. The protective material is generally the material of a laboratory coat or protective gloves. The substrate is spotted, sprayed or impregnated with a solution of indicator compound (e.g., phenanthrene), then allowed to dry under an infrared heating lamp. Once dry, the transparent layer is permanently applied using a securing means such as a binding agent. The transparent layer acts as a protective cover for the indicator compound as well as an optically transparent window to allow for direct spectral analysis of the indicator compound. The indicator-treated substrate and the transparent layer are adhered to one another with the securing means on the outer edges of the patch, exposed. The securing means binds to the article of protective clothing when applied. The patch is placed on the inner surface of the article of protective clothing, in a place that would be susceptible to exposure, in order to monitor for permeation of a chemical lacking the necessary spectral characteristics, previously mentioned. An alternate method of making the patch is to spray on a coating of the transparent layer directly over the indicator-treated substrate. Then a securing means is applied to the outer edges of the patch.

Figure 11:
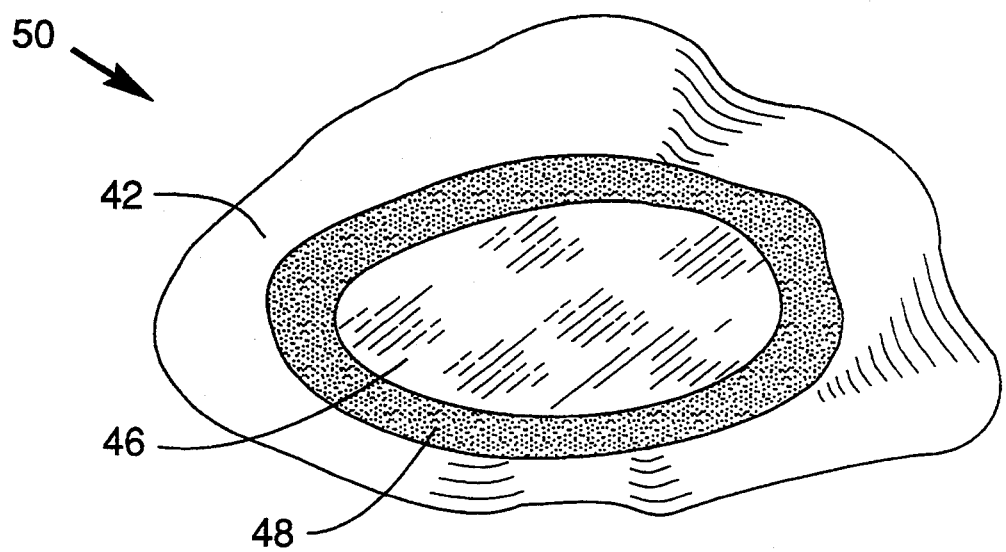
FIG. 11 is a planar view of a patch, adhered to the inner surface of an article of protective clothing.

FIG. 11 is a planar view of the patch, looking directly down on it from the inside of the article of protective clothing. The protective material 42 is shown with the patch adhered in place with the securing means 48 on the outer edges and the transparent layer 46 covering up the indicator-treated substrate underneath. The substrate is against the protective material.

Figure 12:
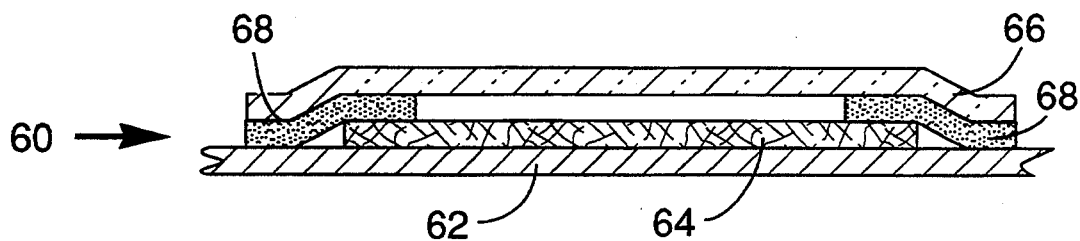
FIG. 12 is another cross-sectional view of a different embodiment of the patch.

FIG. 12 illustrates a cross-sectional view of another embodiment of the patch. The figure shows the protective material 62 with the patch adhered to its surface in which the securing means 68 is sandwiched in between the outermost edges of the indicator-treated substrate 64 and the transparent layer. The securing means and the transparent layer are extended on out to the outer edges of the patch so the securing means is exposed in order to be applied to the protective material. The patch, when attached to the article of protective clothing, acts as a dosimeter badge to detect the permeation of hazardous or toxic vapors or liquids. At the end of the exposure period, when the article of protective clothing is shed from the wearer's body, the indicator compound is then analyzed for luminescence quenching. Using the optically transparent window, the luminescence measurements are made with a portable luminescence monitor.

While there has been shown and described what are at present considered the preferred embodiments of the invention, it will be obvious to those skilled in the art that various changes and modifications can be made therein without departing from the scope of the invention defined by the appended claims.

What is claimed is:

1. Apparatus for detecting the permeation of a chemical through a material, comprising:
   a. a material having a first surface and a second surface, said first surface having been treated with an indicator having luminescent characteristics which are modified upon contact with said chemical, said second surface being in contact with said chemical;
   b. contacting means for contacting said second surface of said material with said chemical; and
   c. analyzing means for determining the modification of luminescent characteristics of said indicator in order to indicate permeation of said chemical through said material.

2. An apparatus in accordance with claim 1 wherein said material comprises protective clothing material.

3. An apparatus in accordance with claim 1 wherein said indicator comprises at least one of phenanthrene and its alkylated derivatives.

4. An apparatus in accordance with claim 1 wherein said analyzing means comprises a spectrofluorometer.

5. Apparatus for detecting the permeation of a chemical through a material, comprising:
   a. a material having a first surface and a second surface, said first surface being adjacent to a substrate, said substrate having been treated with an indicator having luminescent characteristics which are modified upon contact with said chemical;
   b. contacting means for contacting said second surface of said material with said chemical; and
   c. analyzing means for determining the modification of luminescent characteristics of said indicator in order to indicate permeation of said chemical through said material.

6. An apparatus in accordance with claim 5 wherein said substrate comprises cellulosic material.

7. An apparatus in accordance with claim 5 wherein said substrate comprises a sorbent material.

8. An apparatus in accordance with claim 5 wherein said indicator comprises at least one of phenanthrene and its alkylated derivatives.

9. An apparatus in accordance with claim 5 wherein said material comprises protective clothing.

10. An apparatus in accordance with claim 5 wherein said contacting means comprises an open-ended cell.

11. An apparatus in accordance with claim 5 wherein said analyzing means comprises a spectrofluorometer.

12. A method for detecting the permeation of a chemical through a material comprising the steps of:
   a. providing a material having a first surface and a second surface;
   b. treating said first surface with an indicator having luminescent characteristics which are modified upon contact with said chemical;
   c. providing a contacting means for contacting said second surface to said chemical; and
   d. determining the modification of luminescent characteristics of said indicator in order to indicate permeation of said chemical through said material.

13. A method in accordance with claim 12 wherein said material comprises protective clothing material.

14. A method in accordance with claim 12 wherein said indicator comprises at least one of phenanthrene and its alkylated derivatives.

15. A method for detecting the permeation of a chemical through a material, comprising the steps of:
   a. providing a material having a first surface and a second surface, said first surface being adjacent to a substrate;
   b. treating said substrate with an indicator having luminescent characteristics which are modified upon contact with said chemical;
   c. contacting said second surface of said material with said chemical; and
   d. determining the modification of luminescent characteristics of said indicator in order to indicate permeation of said chemical through said material.

16. A method in accordance with claim 15 wherein said substrate comprises cellulosic material.

17. A method in accordance with claim 15 wherein said substrate comprises a sorbent material.

18. A method in accordance with claim 15 wherein said indicator comprises at least one of phenanthrene and its alkylated derivatives.

19. A method in accordance with claim 15 wherein said material comprises protective clothing material.

20. A method in accordance with claim 15 wherein said contact of second surface of said material with said chemical is accomplished through the use of an open-ended cell.

* * * * *